US011622986B2

(12) United States Patent
Nice

(10) Patent No.: US 11,622,986 B2
(45) Date of Patent: Apr. 11, 2023

(54) MOISTURIZING GEL FOR PREVENTING OR HEALING INJURED NIPPLES OR AREOLA IN MY MAMMALIAN FEMALES

(71) Applicant: Frank J. Nice, Derwood, MD (US)

(72) Inventor: Frank J. Nice, Derwood, MD (US)

( * ) Notice: Subject to any disclaimer, the term of this patent is extended or adjusted under 35 U.S.C. 154(b) by 0 days.

(21) Appl. No.: 17/028,656

(22) Filed: Sep. 22, 2020

(65) Prior Publication Data

US 2022/0088104 A1 Mar. 24, 2022

(51) Int. Cl.

*A61K 36/534* (2006.01)
*A61K 47/34* (2017.01)
*A61K 9/06* (2006.01)

(52) U.S. Cl.

CPC .............. *A61K 36/534* (2013.01); *A61K 9/06* (2013.01); *A61K 47/34* (2013.01)

(58) Field of Classification Search

None

See application file for complete search history.

(56) References Cited

U.S. PATENT DOCUMENTS

2012/0014883 A1* 1/2012 Scott ........................ A61P 31/02 424/53
2017/0071874 A1* 3/2017 Aranki .................. A61K 36/53

* cited by examiner

*Primary Examiner* — Melissa S Mercier
(74) *Attorney, Agent, or Firm* — David W Barman

(57) ABSTRACT

The present invention provides a composition and method for preventing or healing injured nipples or areolas in mammalian females utilizing components of water, peppermint oil and poloxamer in a synergistic ratio.

6 Claims, No Drawings

MOISTURIZING GEL FOR PREVENTING OR HEALING INJURED NIPPLES OR AREOLA IN MY MAMMALIAN FEMALES

BACKGROUND OF THE INVENTION

The present invention relates to a formula of all-natural ingredients and a housing for said formula for preventing or healing sore, irritated, damaged, painful, or infected nipples or areolas in mammalian females.

The continued increase in awareness of the physical and emotional benefits of breastfeeding for the mother and baby has helped to increase the number of mothers who initiate breastfeeding. These benefits include increased protection of the infant from illness through the development of protective antibodies, decreased risk of developing childhood cancers, avoiding potential allergies to commercial infant formulas, and enhanced jaw, teeth, and speech development. Furthermore, it has been suggested that nursing mothers have a lower risk of developing breast cancer. Breastfeeding has also been suggested to improve the emotional bond between mother and child. The initiation rate for breastfeeding is somewhere between 70%-80% of new mothers. The healthcare community has also become much more aware of the benefits of breastfeeding in recent years and has become much more proactive in their efforts to help new mothers succeed in their breastfeeding experience.

Nipple/areola soreness, irritation, pain, and damage are very common problems faced by new mothers worldwide after they give birth. It is demonstrated in clinical studies that between 85%-90% of new mothers deal with nipple/areola pain and soreness. Clinical tests demonstrate that many new mothers quit breastfeeding when confronted with these challenges due to the pain and health complications associated with these issues. Causes of nipple soreness, irritation, etc. include, improper positioning of the infant on the mothers breast when breastfeeding and wet saturated breast pads kept on the nipple for extended periods of time, as well as others.

Another significant issue facing lactating mothers is breast infections. One of the most prevalent infections is mastitis, a bacterial infection that mothers experience after they give birth. Mastitis can be caused by plugged milk ducts and cracked nipples, for example. Topical medications and antibiotics are typically provided to help fight the infection.

A second infection faced by breastfeeding mothers is thrush. Thrush is a yeast infection (a fungus) of the infant mouth, which is then passed to the mother during breastfeeding. Thrush can occur when antibiotics are provided to the mother after giving birth, especially after a cesarean section.

Nipple soreness, irritation, damage, pain, and infection require a great deal of time and effort by both the healthcare professional and the mother to treat effectively. The mother is also confronted with the cost of treating these problems, as well as living with the discomfort. Thus, healthcare professionals struggle to find sufficient solutions to help new mothers, whether they are breastfeeding or not, overcome these issues. New solutions are very important in the effort to promote a long and successful breastfeeding experience for as many new mothers as possible. The current methods available to healthcare professionals and new mothers all fall short of alleviating and/or remedying the issues of sore, irritated, damaged, painful, or infected nipples/areolas.

Current topical products designed to alleviate problems associated with nipple/areola soreness, irritation, damage, pain or infection include potentially harmful chemicals or only serve to lessen the soreness, irritation, damage, pain or infection, while ignoring the compounds adverse effects on nursing children.

Therefore, there continues to be a need for a method that effectively prevents and/or heals sore, irritated, damaged, painful, or infected nipples/areolas, and also has the ability to deliver an analgesic effect to the mammalian mother while also being safe, natural, and calming to the nursing mammalian infant.

SUMMARY OF THE INVENTION

The configuration of the present invention provides a specific compound of ingredients, combined in a particular way, housed in a container with an effective delivery system, which is applied to the nipple and areola of a mammalian female.

The present invention contemplates the following as representative improvements over existing gels and balms:

All natural ingredients

A gel which changes state from a solid to a liquid upon cooling, thereby providing an additional analgesic effect.

A delivery system consisting or either:

a) twist on top, polypropylene container with a large opening providing for easy application via a hand scooping the material b) A plastic, glass or acrylic pump bottle which is applied directly to the affected area, or to the hand, which is then applied to the affected area.

Comprised by volume of 81.1% H20, 18.7% Poloxamer 407, and 0.2% Peppermint Oil.

In one embodiment, the present invention is a dermatological composition for preventing or healing injured nipples or areolas in mammalian females, said method comprising:

Water;

Peppermint Oil;

Poloxamer 407; said composition in a synergistic ration of H2O 1:Poloxamer 407 0.20-0.25:Peppermint Oil 0.0020-0.0027.

In one embodiment, the synergistic ratio is

H2O 1:Poloxamer 407 0.23-0.24:Peppermint Oil 0.0023-0.0025.

In one embodiment, the synergistic ratio is

H2O 1:Poloxamer 407 0.22-0.24:Peppermint Oil 0.0024-0.0025.

The present invention includes a method of preparing a dermatological composition as recited herein used as a skin cream or balm, said comprising the following steps:

- placing 10 gm of Poloxamer 407, N.F. into a 4 oz. glass mortar;
- adding and triturating 20 mL of cold Water for Injection (WATER USP) is with a pestle until uniform;
- scraping of the pestle will be necessary with the wetted Poloxamer being returned to the mortar;
- adding and triturating an additional 20 mL of cold WATER USP is added and triturated again until uniform. 2 mL of drawing Peppermint Oil, USP into a glass syringe and adding to the content of the mortar and mixed until uniform;
- adding an additional 30 ml of cold WATER USP until the mixture becomes smooth and milky in appearance;
- transferring the mixture to a one liter, wide-mouth bottle with screw cap;
- adding 60 mL cold WATER USP to the mortar and swirling with the pestle to rinse, subsequently adding to the one liter bottle;

adding an additional 700 mL of cold WATER USP is added to the one liter bottle, a cap is secured tightly one the one liter bottle, and shaken vigorously for 30 seconds;

adding 220 gm of Poloxamer 407 to the one-liter bottle, the cap secured tightly, and shaken vigorously for 30 seconds;

placing the one liter bottle into a 4 degree C. refrigerator for one hour;

removing the bottle is removed after one hour, shaking the bottle vigorously for 30 seconds and returning to the refrigerator;

optionally, repeating said removing the bottle is removed after one hour, shaking the bottle vigorously for 30 seconds and returning to the refrigerator until all Poloxamer 407 is dissolved, the solution is clear, and most of the bubbles have dispersed;

removing the one-liter bottle from the refrigerator and adding Poloxamer 407 is added to bring the total volume.

This method of preparation includes scaling for desired amounts.

The invention includes method of treating, preventing or ameliorating skin anomalies of the nipple and areola of a mammal comprising the steps of Providing a composition of claim 1;

Applying 0.1 ml directly on the nipple, areola, of both;

Repeating said applying 0.1 ml between two and ten times per day over 2 to 30 days.

In one embodiment, the present invention is a dermatological composition for preventing or healing injured nipples or areolas in mammalian females, consisting of:

Water;

Peppermint Oil;

Poloxamer 407; said composition in a synergistic ration of H2O 1:Poloxamer 407 0.20-0.25:Peppermint Oil 0.0020-0.0027.

In one embodiment, the synergistic ratio is consisting of: H2O 1:Poloxamer 407 0.23-0.24:Peppermint Oil 0.0023-0.0025

In one embodiment, the synergistic ratio is consisting of: H2O 1:Poloxamer 407 0.22-0.24:Peppermint Oil 0.0024-0.0025

DETAILED DESCRIPTION OF THE PREFERRED EMBODIMENT

Although as presented herein a specific bath size is presented, it is contemplated that amounts are adjusted for larger scale as desired.

After significant experimentation involving a plurality of components, the present invention arrives at a synergistic ratio viewed to be clinically effective.

H2O:Poloxamer 407:Peppermint Oil as the most effective composition.

H2O 1:Poloxamer 407 0.20-0.25:Peppermint Oil 0.0020-0.0027

In a preferred embodiment, the synergistic ratio is

H2O 1:Poloxamer 407 0.23-0.24:Peppermint Oil 0.0023-0.0025

In another preferred embodiment, the synergistic ratio is H2O 1:Poloxamer 407 0.22-0.24:Peppermint Oil 0.0024-0.0025

Although the components are also expressed as percentage With one preferred composition by volume of 81.1% H20, 18.7% Poloxamer 407, and 0.2% Peppermint Oil.

The composition is more than merely routine experimentation as the impetus to provide the therapeutic effect required a significant number of components and the final formula is based on synergistic effect as opposed to preferred percentages.

Chemical & Physical Properties of Peppermint Oil (CAS 8006-90-4) Peppermint Oil is the volatile oil distilled with steam from the fresh over ground parts of the flowering plant of Mentha 170 piperitaLinne (Fam. Labiatae), rectified by distillation and neither partially nor wholly dementholized. It yields not less than 5.0 percent of esters, calculated as methyl acetate (C12H2202), and not less than 50.0 percent of total menthol (CloH200), free and as esters.

Chemical and Physical Properties of Poloxamer 407 (CAS 9003-11-6):

Poloxamers are nonionic triblock copolymers composed of a central hydrophobic chain of polyoxypropylene (poly (propylene oxide)) flanked by two hydrophilic chains of polyoxyethylene (poly(ethylene oxide)). The word "poloxamer" 235 was coined by the inventor, Irving Schmolka, who received the patent for these materials in 1973. Poloxamers are also known by the trade names Synperonics, Pluronics, and Kolliphor. Because the lengths of the polymer blocks can be customized, many different poloxamers exist that have slightly different properties. For the generic term "poloxamer", these copolymers are commonly named with the letter "P" (for poloxamer) followed by three digits: the first two digits×100 give the approximate molecular mass of the polyoxypropylene core, and the last digit×10 gives the percentage polyoxyethylene content (e.g., P407 Poloxamer with a polyoxypropylene molecular mass of 4,000 g/mol and a 70% polyoxyethylene content).

The configuration of the present invention provides a specific compound of ingredients, combined in a particular way, housed in a particular application vessel, which is applied to the nipple and areola of a mammalian female.

Preferred Method of Manufacture:

10 gm of Poloxamer 407, N.F. is placing into a 4 oz. glass mortar. 20 mL of cold Water USP is added and triturated with a pestle until uniform.

Periodic scraping of the pestle will be necessary with the wetted Poloxamer being returned to the mortar.

An additional 20 mL of cold WATER USP is added and triturated again until uniform.

2 mL of Peppermint Oil, USP is drawn up into a glass syringe and added to the content of the mortar and mixed until uniform.

An additional 30 ml of cold WATER USP is added and mixed until the mixture becomes smooth and milky in appearance.

The mixture is transferred to a one liter, wide-mouth bottle with screw cap.

60 mL cold WATER USP is added to the mortar and swirled with the 290 pestle to rinse, and then added to the one liter bottle.

An additional 700 mL of cold WATER USP is added to the one liter bottle, the cap secured tightly, and shaken vigorously for 30 seconds.

220 gm of Poloxamer 407 is added to the one liter bottle, the cap secured tightly, and shaken vigorously for 30 seconds.

The one liter bottle is then placed into a 4 C refrigerator for one hour.

The bottle is removed after one hour, shaken vigorously for 30 seconds and returned to the refrigerator.

This process is repeated until all Poloxamer 407 is dissolved, the solution is clear, and most of the bubbles have dispersed.

The one-liter bottle is removed from the refrigerator and Poloxamer 407 is added to bring the total volume to 1,000 mL.

The bottle is closed, shaken vigorously for 30 seconds, and returned to the refrigerator.

Once all the bubbles have dispersed and the Poloxamer 407 has dissolved the bottle is removed from the refrigerator and packaged in its individual 60 ml bottles for shipping.

The resultant composition exhibits a turbidity at or within 5% of Deionized water.

IN a preferred embodiment, the resultant composition of the present invention has Dynamic a dynamic viscosity at 25 degrees Celsius of 1000 to 9000 mPa·s In one embodiment, 0.1 mL is applied four to ten times per day for 2 to 30 days.

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

I claim:

1. A dermatological composition for preventing or healing injured nipples or areolas in mammalian females, consisting of:

water;

peppermint oil;

poloxamer 407; said composition in a ratio of water 1:poloxamer 407 0.20-0.25: peppermint oil 0.0020-0.0027.

2. The composition of claim 1 wherein the ratio is water 1: poloxamer 407 0.23-0.24: peppermint oil 0.0023-0.0025.

3. The composition of claim 1 wherein the ratio is water 1: poloxamer 407 0.22-0.24: peppermint oil 0.0024-0.0025.

4. A method of preparing a dermatological composition as recited in claim 1 used as a skin cream or balm, said method consisting of the following steps:

placing 10 gm of poloxamer 407, N.F. into a 4 oz. glass mortar;

adding and triturating 20 mL of cold Water for Injection (water USP) is with a pestle until uniform;

scraping of the pestle will be necessary with the wetted Poloxamer being returned to the mortar;

adding and triturating an additional 20 mL of cold water USP is added and triturated again until uniform 2 mL of drawing, peppermint oil USP into a glass syringe and adding to the content of the mortar and mixed until uniform;

adding an additional 30 ml of cold water USP until the mixture becomes smooth and milky in appearance;

transferring the mixture to a one liter, wide-mouth bottle with screw cap;

adding 60 mL cold water USP to the mortar and swirling with the pestle to rinse, subsequently adding to the one liter bottle;

adding an additional 700 mL of cold water USP is added to the one liter bottle, a cap is secured tightly one the one liter bottle, and shaken vigorously for 30 seconds;

adding 220 gm of poloxamer 407 to the one-liter bottle, the cap secured tightly, and shaken vigorously for 30 seconds;

placing the one liter bottle into a 4 degree C. refrigerator for one hour;

removing the bottle is removed after one hour, shaking the bottle vigorously for 30 seconds and returning to the refrigerator;

optionally, repeating said removing the bottle is removed after one hour, shaking the bottle vigorously for 30 seconds and returning to the refrigerator until all poloxamer 407 is dissolved, the solution is clear, and most of the bubbles have dispersed;

removing the one-liter bottle from the refrigerator and adding poloxamer 407 is added to bring the total volume.

5. A method of treating, preventing or ameliorating skin anomalies of the nipple and areola of a mammal said method consisting of the steps:

providing a composition of claim 1;

applying 0.1 ml directly on the nipple, areola, of both;

repeating said applying 0.1 ml between two and ten times per day over 2 to 30 days.

6. A dermatological composition for preventing or healing injured nipples or areolas in mammalian females, consisting of:

water;

peppermint oil;

poloxamer 407; said composition in a ratio of:

water 1: poloxamer 407 0.20-0.25: peppermint oil 0.0020-0.0027, whereby said composition is a gel which changes state from a solid to a liquid upon cooling.

* * * * *